United States Patent [19]

Wolpers et al.

[11] Patent Number: 5,442,099

[45] Date of Patent: Aug. 15, 1995

[54] BIS-(THIOBENZOYLDISULFIDO)-ALKANES

[75] Inventors: Juergen Wolpers, Haltern; Karl-Heinz Nordsiek, Marl; Jaroslaw Monkiewicz, Marl; Dieter Zerpner, Marl, all of Germany

[73] Assignee: Huels Aktiengesellschaft, Marl, Germany

[21] Appl. No.: 152,702

[22] Filed: Nov. 16, 1993

[30] Foreign Application Priority Data

Dec. 9, 1992 [DE] Germany ............ 42 41 447.4

[51] Int. Cl.⁶ ......................................... C07C 327/36
[52] U.S. Cl. ................................................. 560/302
[58] Field of Search ......................................... 560/302

[56] References Cited

FOREIGN PATENT DOCUMENTS 3941002 6/1991 Germany .

Primary Examiner—Christopher Henderson

Attorney, Agent, or Firm—Oblon, Spivak, McClelland, Maier & Neustadt

[57] ABSTRACT

Polysulfide compounds and vulcanization compositions containing the polysulfide compounds, for use in vulcanizing rubbers, are disclosed, with the polysulfide compounds being of the formula

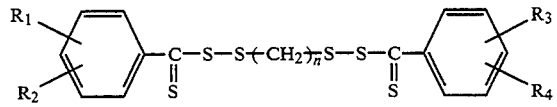

wherein $R^1$-$R^4$ are each, independently, hydrogen or $C_1$-$C_4$ alkyl and n is 2 to 10 wherein the polysulfide compounds can be used alone or in a vulcanization composition containing the polysulfide compound, sulfur, one or more additional accelerators, one or more basic compounds and, optionally, conventional rubber additives, to provide vulcanized products with improved reversion stability and ageing stability.

1 Claim, No Drawings

BIS-(THIOBENZOYLDISULFIDO)-ALKANES

BACKGROUND OF THE INVENTION

Field of the Invention

The present invention relates to novel polysulfide compounds of aromatic dithiocarboxylic acids and their use as nitrosamine-free crosslinking agents and in vulcanization systems for improving the reversion stability and ageing stability of diene rubbers.

Discussion of the Background

The crosslinking of rubber with sulfur or sulfur donors and accelerator systems generally provides vulcanized products whose polymer chains in the initial phase are linked by polysulfidic sulfur networks. Polysulfidically crosslinked vulcanized products lead to good results with regard to a large number of properties. In addition to mechanical strength, this applies in particular to the tear propagation resistance and abrasion resistance of the vulcanized product. However, such sulfur-containing systems often suffer from the disadvantage of the reversion process. The term reversion covers not only the deterioration of the vulcanizate properties during the vulcanization process, but also duping anaerobic aging under dynamic stress. The sulfur liberated during reversion accumulates on polymer segments and thus increases their glass transition temperature $T_g$, while at the same time catalyzing the attack on the vulcanized product by oxygen. Both effects cause damage to the network. The stated secondary reactions of the sulfur, which begin during the vulcanization process itself, depending on reaction time and reaction temperature, substantially reduce the performance limits of the elastomer and therefore necessitate restrictions with regard to the optimum design of the production process.

The use of so-called EV systems has been proposed for reducing the secondary reactions of the sulfur. These are systems which consist of increased amounts of vulcanization accelerators in conjunction with minimum amounts of sulfur. Due to the more rapid initial vulcanization, however, the safety during processing is adversely affected. In addition, and more importantly, there is the inevitable deterioration in abrasion resistance, tear propagation resistance and cord adhesion, particularly with regard to tire technology (cf. P. M. Lewis, NR Technologie 17 (4)1 1986, page 60).

German Patent 3,941,002 proposes, inter alia, polysulfide derivatives having substituted hydroxydithiobenzoates as leaving groups. These complex structured compounds possess serious disadvantages. Owing to the high molecular weight, it is necessary, as is evident from the Examples in the German Patent, to use 7 parts of crosslinking agent per 100 parts of rubber in order to obtain vulcanized products having acceptable level of properties. In addition to being economically unacceptable, extremely undesirable blooming phenomena tend to occur due to the very limited solubility of such compounds.

The poor solubility and high melting point of the substances mentioned in DE 3,941,002 also lead to difficulties in mixing and thus to poor dispersion of the substance in the rubber mixture, with all its attendant adverse consequences.

Thus, vulcanization agents and methods are needed which overcome the above-noted deficiencies while providing improved reversion stability and aging stability in the resultant vulcanized products.

SUMMARY OF THE INVENTION

Accordingly, one object of the present invention is to provide a vulcanization agent which avoids the disadvantages of EV systems and does not contain nitrosamine-forming substances.

A further object of the present invention is to provide a vulcanization agent which provides improved reversion stability and aging stability.

A further object of the present invention is to provide a vulcanization method which avoids the disadvantages of EV systems and does not result in the formation of nitrosamines, which utilizes the vulcanization agent of the present invention.

A further object of the present invention is to provide a vulcanization composition for use in providing the advantages denoted above.

These and other objects of the present invention have been satisfied by the discovery of polysulfide compounds of the formula

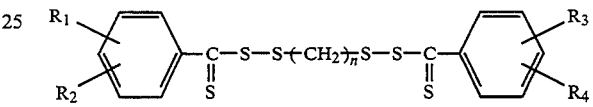

wherein $R_1$-$R_4$ are each, independently, hydrogen or $C_1$-$C_4$ alkyl and n is an integer from 2 to 10, and their use in vulcanization compositions to obtain vulcanized products having improved reversion stability and aging stability.

DETAILED DESCRIPTION OF THE PREFERRED EMBODIMENTS

Polysulfide compounds of the present invention are low-melting and have good solubility in diene rubber mixtures. When the groups $R_1$-$R_4$ each have low molecular weights (<29 g/mol) and n has a low to medium value between 2 and 10, the molecular weight of the vulcanization agent is also sufficiently low to necessitate a substantially smaller amount for effecting vulcanization.

Preferred substituents $R_1$-$R_4$ are hydrogen or a methyl group, where the position of the methyl group may be ortho, meta or para to the thiocarbonyl group. The alkylene bridge may be between 2 and 10 carbon atoms long, with compounds having $C_2$- or $C_6$-chains being preferred. In the vulcanization reaction, the leaving group of the polysulfide compounds is $ARCS_2^\ominus$ with Ar being either $(R^1)(R^2)C_6H_3$- or $(R^3)(R^4)C_6H_3$-. Depending on the chain length, the polysulfide compounds represent liquid to low-melting solid substances which can be readily incorporated into rubber mixtures.

Preferred examples of polysulfide compounds according to the present invention include bis-1,6-(thiobenzoyldisulfido)-ethane and -hexane, referred to hereafter as BTBDE and BTBDH. The polysulfide compounds can be used as crosslinking agents in pure form, as concentrated mixtures in rubbers (so-called batches) or as mixtures with fillers.

If the polysulfide compounds are used alone for vulcannation, 4 to 6 parts by weight, preferably 4.5–5.5 parts, are sufficient for achieving the effect according to the invention (based on the amount of rubber being vulcanized). For example, a vulcanized product having a tensile stress of 6.8 MPa at 300% elongation is obtained from 5.7 parts of the compound polysulfide of the present invention, wherein $R_1$–$R_4$=H and n=6 (BTBDH), per 100 parts of rubber.

Furthermore, it has been found that the required amount of polysulfide compounds of the present invention can be further reduced if required when they are used in special vulcanization compositions. These vulcanization compositions are mixtures of polysulfide compounds of the present invention, which also contain very small amounts of sulfur, one or more additional accelerators and furthermore a basic substance. When these vulcanization compositions are used, the reversion behavior and ageing behavior of the resultant vulcanized products are not adversely affected, as might be expected based on processes using conventional vulcanization agents. Surprisingly the opposite effect is obtained, with the reversion process being completely suppressed and the aerobic ageing resistance, (the retention of the physical properties after hot-air aging) being substantially improved. As a result, vulcanized products of diene rubbers having very high reversion resistance and ageing resistance are obtained.

Substantially smaller amounts of the polysulfide compounds are sufficient for conventional crosslinking if, in addition to only 0.5 to 4 parts by weight, preferably 0.5 to 2.5 parts, of BTBDH or BTBDE, an amount of 0 to 0.3 part by weight, preferably 0 to 0.1 parts of sulfur, 1 to 2.5 parts, preferably 1–1.5 parts, of an additional accelerator, such as a conventional sulfenamide or mercapto accelerator or a combination thereof, and 0.5 to 4 parts by weight, preferably 0.5 to 1.5 parts, of a basic compound, are added (based in each case on 100 parts of rubber). As a result of these additives, the tendency of diene rubbers to undergo reversion is completely suppressed and the aerobic ageing is substantially improved.

Any conventional mercapto or sulfenamide accelerator may be used as the additional accelerator, with zinc 2-mercaptobenzothiazole (ZMBT), dibenzothiazyl disulfide (MBTS) and N-tert-butyl-2-benzothiazylsulfenamide (TBBS) being preferred.

According to the invention, the polysulfide compounds are used for vulcanization not only without sulfur but also with sulfur in amounts of up to 0.3 part by weight, preferably up to 0.1 part, per 100 parts of rubber. Use of the polysulfide compounds of the present invention in the presence of sulfur results in an increase in the crosslinking yield, without adversely affecting the reversion or aging behavior of the resultant vulcanized product, when the amounts are kept within the prescribed range. However, reversion and unfavorable ageing properties are increasingly observed with amounts of sulfur greater than 0.3 part by weight.

The basic substances used in the composition of the present invention suppress the reversion process, improve the aging properties and increase the crosslinking yield. Suitable basic compounds include guanidine compounds, such as diphenylguanidine. Salts of dithiocarbamic acids are also suitable, but care must be taken to use carbonates of so-called "safe amines" which do not develop nitrosamines. The zinc salt of dibenzyldithiocarbamic acid is an example of such a "safe amine" derived salt.

Conventional rubber additives may also be used as needed, such as fillers, plasticizers, tackifiers, accelerators, activators, stearic acid, wax, anti-aging agents and antiozonants, blowing agents, dyes and pigments. The preparation of the vulcanization composition of the present invention containing the above rubber additives can be carried out using conventional processes known to a person skilled in the art.

The vulcanization process itself is carried out at temperatures between 130° and 250° C., preferably between 150° and 220° C., according to conventional vulcanization procedures.

When used in the vulcanization compositions of the present invention, the polysulfide compounds of the present invention provide advantages with regard to reversion stability after relatively long vulcanization time and/or relatively high vulcanization temperature, while providing, at the same time, a considerably smaller decrease in efficiency in the aerobic ageing of elastomers.

Having generally described this invention, a further understanding can be obtained by reference to certain specific examples which are provided herein for purposes of illustration only and are not intended to be limiting unless otherwise specified.

1. Sodium dithiobenzoate

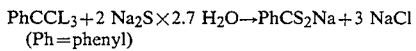
$PhCCL_3 + 2\ Na_2S \times 2.7\ H_2O \rightarrow PhCS_2Na + 3\ NaCl$
(Ph=phenyl)

415 g of sodium sulfide hydrate were suspended in 1,000 ml of methanol and heated to reflux temperature. Thereafter, 330.4 g of benzotrichloride were added dropwise under reflux and the reaction mixture allowed to continue reacting for a further few minutes at the boiling point. The precipitated NaCl was then separated off at room temperature. The methanol was evaporated off at 50° C. and the remaining residue was dissolved in about 1,900 ml of distilled water. For purification, this aqueous phase (2,200 ml) was extracted with 500 ml of toluene and the separated toluene phase was discarded.

2. 1,6-Bis(sodium thiosulfato)hexane

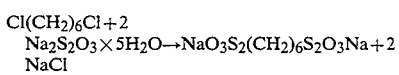
$Cl(CH_2)_6Cl + 2\ Na_2S_2O_3 \times 5H_2O \rightarrow NaO_3S_2(CH_2)_6S_2O_3Na + 2\ NaCl$ 108.5 g of 1,6-dichlorohexane were added to a solution of 374.5 g of sodium thiosulfate pentahydrate in about 1,150 ml of water at room temperature. The reaction mixture was then adjusted to a pH of 7 to 8 by the dropwise addition of 5% aqueous NaOH. At the same time, the total content of the flask was heated to the reflux temperature and stirred for 7–8 hours at that temperature. Thereafter, the mixture was cooled to room temperature and extracted with 150 ml of methyl tert-butyl ether (MTB). The MTB extract was discarded and the aqueous solution of 1,6-bis(sodium thiosulfato)hexane (about 1,500 ml) was used in the next stage.

3. 1,6-Bis(thiobenzoyldisulfido)hexane

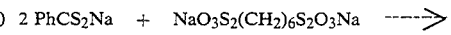
$2\ PhCS_2Na\ +\ NaO_3S_2(CH_2)_6S_2O_3Na \longrightarrow$

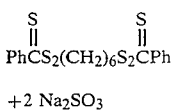

$$\underset{\underset{\|}{S}}{Ph}CS_2(CH_2)_6S_2\underset{\underset{\|}{S}}{C}Ph$$

$+2\ Na_2SO_3$

The individual reaction components were introduced in the following order, at room temperature, into a 5 l flask having a stirrer, a dropping funnel and pH measuring electrode:
  a) 1,500 ml of the solution of 1,6-bis(sodium thiosulfato)hexane (Example 2)
  b) 100 g of 37% modulus formalin solution
  c) 2,200 ml of sodium dithiobenzoate solution (Example 1).

The pH was adjusted to pH 8 by the dropwise addition of 10% HCl with very vigorous stirring. The reaction mixture was stirred vigorously for 7 hours at room temperature and pH 7–8. A dark red oil was formed and was separated from the aqueous phase after the end of the reaction. The oil phase was diluted with 1,500 ml of toluene and washed 3 times with about 700 ml of H$_2$O. The organic phase was dried over magnesium sulfate (sodium sulfate). After the drying agent had been filtered off under suction, the toluene was evaporated in vacuo. 220 g of the product remained in the form of a dark red viscous oil; yield 70%.

Example 1 demonstrates the use of BTBDH in a natural rubber formulation. Compared with Comparative Example 1 (the same natural rubber base mixture with a conventional vulcanization system comprising two parts of sulfur and one part of the sulfenamide accelerator CBS), the following are found:
  a) improved crosslinking activity of the composition according to the present invention,
  b) surprisingly short initial vulcanization and complete vulcanization times, even at 150° C., using the composition of the present invention, and
  c) substantially improved ageing-stability of the composition of the present invention, relative to the Comparative Example.

Example 2 demonstrates the use of 3.5 parts of BTBDH in combination with 1.5 parts of MBTS as an additional accelerator and 1.5 parts of ZBEC as the basic compound—but without sulfur—in a cis-polyisoprene formulation. With a substantially reduced amount of the vulcanization agent according to the invention, the resulting tensile stress of the vulcanization product is nevertheless higher than in Example 1. This is surprising since the additionally used substances MBTS and ZBEC do not themselves display any vulcanization activity. In this context, see also Comparative Example II which, in spite of a substantially larger amount of sulfur, gives an inadequate modulus.

Example 3 demonstrates the use of only 2 parts of BTBDH in the same base mixture as in Example 2, but with 0.2 part of sulfur and 1.5 parts of MBTS as an additional accelerator and one part of ZBEC as a basic substance. In this composition, a retention of 72% of the original elongation at break of the vulcanized product is observed after ageing for 14 days at 100° C.

Example 4 describes the use of diphenylguanidine (DPG) as basic substance, in addition to TBBS as an additional accelerator. A vulcanized product having very high dynamic stability, which does not deteriorate even in the case of ageing for 14 days at 100° C., is obtained. The retention of the elongation at break is 73%.

Example 5 describes the use of only 0.5 part of BTBDH together with 0.3 part of sulfur, 2 parts of TBBS as an additional accelerator and 1.5 parts of ZBEC as a basic substance. A vulcanized product having a modulus (tensile stress at 300% elongation) of 0.8 MPa is obtained. After ageing for 14 days at 100° C., the vulcanized product exhibits 71% retention of the elongation at break.

The various embodiments of the process according to the invention which have been described above only with reference to some examples demonstrate the extraordinary properties of the vulcanized products achieved using the vulcanization compositions of the present invention, even in the case of a rubber such as cis-polyisoprene, which is extremely sensitive and not very resistant to ageing under normal conditions.

Explanations for the Tables:
1) RSS #1 Defo 1000
2) NATSYN ®, Goodyear
3) N-Isopropyl-N'-phenyl-p-phenylenediamine (IPPD)
4) N-(1,3-Dimethylbutyl)-N'-phenyl-p-phenylenedismine (GPPD)
5) N-Cyclohexyl-1-benzothiazylsulfenamide (CBS)
6) N-tert-Butyl-2-benzothiazylsulfenamide (TBBS)
7) Dibenzothiazlyl disulfide (MBTS)
8) Diphenylguanidine (DPG)
9) Zinc dibenzyldithiocarbamate (ZBEC)
10) Bis-1,6-(thiobenzoyldisulfido)-hexane (BTBDH)
': Time in minutes after which the ball was destroyed under the stated conditions.

TABLE 1

| Example | | 1 | 2 | 3 | 4 | 5 |
|---|---|---|---|---|---|---|
| Natural rubber[1)] | | 100.0 | — | — | — | — |
| cis-Polyisoprene[2)] | | — | 100.0 | 100.0 | 100.0 | 100.0 |
| ZnO RS | | 3.0 | 3.0 | 3.0 | 3.0 | 3.0 |
| Stearic acid | | 2.0 | 2.0 | 2.0 | 2.0 | 2.0 |
| IPPD[3)] | | 1.0 | 1.0 | 1.0 | 1.0 | 1.0 |
| 6PPD[4)] | | 1.0 | 1.0 | 1.0 | 1.0 | 1.0 |
| Corax N-339 | | 45.0 | 45.0 | 45.0 | 45.0 | 45.0 |
| CBS[5)] | | — | — | — | — | — |
| Sulfur | | — | — | 0.2 | 0.3 | 0.3 |
| TBBS[6)] | | — | — | — | 1.5 | 2.0 |
| MBTS[7)] | | — | 1.5 | 1.5 | — | — |
| DPG[8)] | | — | — | — | 3.0 | — |
| ZBEC[9)] | | — | 1.5 | 1.0 | — | 1.5 |
| BTBDH[10)] | | 5.7 | 3.5 | 2.0 | 3.0 | 0.5 |
| Vulcameter 150° C. | t$_{10}$ min. | 1.9 | 1.3 | 1.5 | 1.0 | 2.5 |
| | t$_{90}$ min. | 4.5 | 14.0 | 11.5 | 8.6 | 11.2 |
| Vulcameter 180° C. | t$_{10}$ min. | 0.8 | 0.6 | 0.7 | 0.5 | 1.0 |
| | t$_{90}$ min. | 1.5 | 5.5 | 5.8 | 3.0 | 2.5 |
| Vulcanization at °C./min. | | 150/30 | 180/10 | 180/10 | 180/10 | 180/10 |
| Tensile strength | MPa | 18.0 | 21.1 | 30.3 | 20.7 | 21.1 |
| Elongation at break | % | 583 | 589 | 579 | 572 | 537 |
| Modulus, 100% elongation | MPa | 1.4 | 1.4 | 1.4 | 1.4 | 1.4 |

TABLE 1-continued

| Example | | | 1 | 2 | 3 | 4 | 5 |
|---|---|---|---|---|---|---|---|
| Modulus, 300% elongation | MPa | | 7.4 | 7.9 | 8.0 | 8.1 | 9.8 |
| Tear strength (Pohle) | N/mm | | 66 | 66 | 68 | 74 | 65 |
| Permanent set | % | | 16 | 9 | 8 | 8 | 8 |
| Hardness | 22° C. | Shore A | — | 56 | 56 | 58 | 57 |
| | 75° C. | | — | 48 | 49 | 48 | 48 |
| Rebound | 22° C. | | — | 51 | 51 | 50 | 48 |
| | 75° C. | | — | 65 | 61 | 64 | — |
| Compr. set 24 h/70° C. | % | | — | 9 | 11 | 11 | 11 |
| Compr. set 24 h/100° C. | % | | — | 27 | 27 | 28 | 34 |
| Vulcanization at 180° C. | min. | | — | 20 | 20 | 20 | 20 |
| Martens ball fatigue | 150N | °C. | — | 86 | 91 | 82 | 86 |
| | 200N | °C. | — | 110 | 120 | 103 | 110 |
| | 250N | °C. | — | 124 | 144 | 120 | 120 |
| | 300N | °C. | — | 139 | 167 | 133 | 145 |
| | 350N | °C. | — | 160 | 6' | 152 | 168 |
| | 400N | °C. | — | 8' | — | 178 | 5' |
| | 450N | °C. | — | — | — | — | — |

| Example | | | Aging for 7 days at 100° C. | | | | |
|---|---|---|---|---|---|---|---|
| | | | 1 | 2 | 3 | 4 | 5 |
| Tensile strength | MPa | | 7.0 | 20.4 | 20.0 | 17.7 | 19.5 |
| Elongation at break | % | | 289 | 428 | 483 | 521 | 443 |
| Modulus, 100% elongation | MPa | | 2.0 | 2.8 | 2.2 | 1.8 | 2.4 |
| Modulus, 300% elongation | MPa | | — | 14.2 | 11.5 | 9.2 | 12.8 |
| Tear strength (Pohle) | N/mm | | 17 | 56 | 55 | 36 | 57 |
| Permanent set | % | | 8 | 9 | 9 | 14 | 9 |
| Hardness | 22° C. | Shore A | — | 63 | 62 | 64 | 63 |
| | 75° C. | | — | 55 | 54 | 58 | 56 |
| Rebound | 22° C. | | — | 54 | 52 | 56 | 52 |
| | 75° C. | | — | 62 | 61 | 65 | 61 |
| Compr. set 24 h/70° C. | % | | — | 17 | 16 | 12 | 15 |
| Compr. set 24 h/100° C. | % | | — | 26 | 33 | 24 | 34 |
| Martens ball fatigue | 150N | °C. | — | 84 | 75 | 78 | 85 |
| | 200N | °C. | — | 111 | 108 | 94 | 103 |
| | 250N | °C. | — | 134 | 132 | 114 | 132 |
| | 300N | °C. | — | 141 | 157 | 134 | 150 |
| | 350N | °C. | — | 156 | 164 | 150 | 170 |
| | 400N | °C. | — | 14.8' | 14.8' | 169 | 5' |
| | 450N | °C. | — | — | — | 12' | — |

| Example | | | Aging for 14 days at 100° C. | | | | |
|---|---|---|---|---|---|---|---|
| | | | 1 | 2 | 3 | 4 | 5 |
| Tensile strength | MPa | | 5.7 | 15.8 | 17.3 | 11.8 | 16.1 |
| Elongation at break | % | | 240 | 331 | 415 | 417 | 380 |
| Modulus, 100% elongation | MPa | | 2.3 | 3.2 | 2.5 | 1.9 | 2.6 |
| Modulus, 300% elongation | MPa | | — | 15.7 | 12.7 | 8.5 | 13.1 |
| Tear strength (Pohle) | N/mm | | 14 | 37 | 41 | 18 | 35 |
| Permanent set | % | | 8 | 7 | 11 | 14 | 9 |
| Hardness | 22° C. | Shore A | — | 62 | 64 | 64 | 65 |
| | 75° C. | | — | 52 | 55 | 55 | 55 |
| Compr. set 24 h/70° C. | % | | — | 23 | 26 | 21 | 20 |
| Compr. set 24 h/100° C. | % | | — | 34 | 39 | 29 | 39 |
| Martens ball fatigue | 150N | °C. | — | 83 | 74 | 72 | 85 |
| | 200N | °C. | — | 109 | 102 | 92 | 101 |
| | 250N | °C. | — | 130 | 128 | 110 | 128 |
| | 300N | °C. | — | 147 | 154 | 122 | 153 |
| | 350N | °C. | — | 14' | 9' | 144 | 13' |
| | 400N | °C. | — | — | — | 158 | — |
| | 450N | °C. | — | — | — | 11' | — |

TABLE 2

| Comparative Example | I | II |
|---|---|---|
| Natural rubber (1) | 100.0 | 100.0 |
| cis-Polyisoprene (2) | — | — |
| ZnO RS | 3.0 | 3.0 |
| Stearic acid | 2.0 | 2.0 |

TABLE 2-continued

| Comparative Example | | | I | II |
|---|---|---|---|---|
| Vulc. 4010 NA (3) | | | 1.0 | 1.0 |
| Vulc. 4020 (4) | | | 1.0 | 1.0 |
| Corax N-339 | | | 45.0 | 45.0 |
| CBS (5) | | | 1.0 | — |
| Sulfur | | | 2.0 | 0.4 |
| TBBS (6) | | | — | 1.2 |
| MBTS (7) | | | — | — |
| DPG (8) | | | — | — |
| ZBEC (9) | | | — | — |
| BTBDH | | | — | — |
| Vulcameter 150° C. | $t_{10}$ min. | | 5.0 | 8.4 |
| | $t_{90}$ min. | | 9.2 | 14.4 |
| Vulcanization at °C./min. | | | 150/30 | 150/30 |
| Tensile strength | MPa | | 19.3 | 19.5 |
| Elongation at break | % | | 480 | 528 |
| Modulus, 100% elongation | MPa | | 1.6 | 1.5 |
| Modulus, 300% elongation | MPa | | 10.5 | 9.2 |
| Tear strength (Pohle) | N/mm | | 37 | 66 |
| Permanent set | % | | 10 | 12 |
| Hardness | 22° C. | Shore A | — | 55 |
| | 75° C. | | — | 44 |
| Rebound | 22° C. | | — | 50 |
| | 75° C. | | — | 58 |
| Compr. set 24 h/70° C. | % | | — | 36 |
| Compr. set 24 h/100° C. | % | | — | — |
| Vulcanization at 180° C. min. | | | — | — |
| Martens | 150N | °C. | — | — |
| ball | 200N | °C. | — | — |
| fatigue | 250N | °C. | — | — |
| | 300N | °C. | — | — |
| | 350N | °C. | — | — |
| | 400N | °C. | — | — |
| | 450N | °C. | — | — |

| Comparative Example | | | Aging for 7 days at 100° C. | |
|---|---|---|---|---|
| | | | I | II |
| Tensile strength | MPa | | 4.5 | 11.1 |
| Elongation at break | % | | 105 | 391 |
| Modulus, 100% elongation | MPa | | — | 1.9 |
| Modulus, 300% elongation | MPa | | 16.0 | 8.9 |
| Tear strength (Pohle) | N/mm | | 1 | 13 |
| Permanent set | % | | — | 11 |
| Hardness | 22° C. | Shore A | — | 61 |
| | 75° C. | | — | 49 |
| Rebound | 22° C. | | — | 46 |
| | 75° C. | | — | 50 |
| Compr. set 24 h/70° C. | % | | — | 28 |
| Compr. set 24 h/100° C. | % | | — | — |
| Martens | 150N | °C. | — | — |
| ball | 200N | °C. | — | — |
| fatigue | 250N | °C. | — | — |
| | 300N | °C. | — | — |
| | 350N | °C. | — | — |
| | 400N | °C. | — | — |
| | 450N | °C. | — | — |

| Comparative Example | | | Aging for 14 days at 100° C. | |
|---|---|---|---|---|
| | | | I | II |
| Tensile strength | MPa | | 3.0 | 66.0 |
| Elongation at break | % | | 54 | 311 |
| Modulus, 100% elongation | MPa | | — | 1.7 |
| Modulus, 300% elongation | MPa | | — | 6.5 |
| Tear strength (Pohle) | N/mm | | 18 | 12 |
| Permanent set | % | | 1 | 10 |
| Hardness | 22° C. | Shore A | — | 60 |
| | 75° C. | | — | 47 |
| Rebound | 22° C. | | — | 42 |
| | 75° C. | | — | 45 |
| Compr. set 24 h/70° C. | % | | — | 40 |
| Compr. set 24 h/100° C. | % | | — | — |
| Martens | 150N | °C. | — | — |
| ball | 200N | °C. | — | — |
| fatigue | 250N | °C. | — | — |
| | 300N | °C. | — | — |
| | 350N | °C. | — | — |
| | 400N | °C. | — | — |
| | 450N | °C. | — | — |

What is claimed as new and desired to be secured by Letters Patent of the United States is:

1. A polysulfide compound of the formula

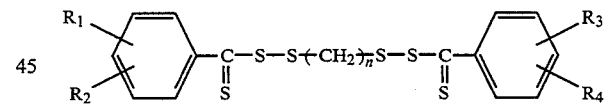

wherein $R_1$–$R_4$ are each hydrogen and n is 2 or 6.

* * * * *